United States Patent [19]

Eckhardt et al.

[11] Patent Number: 4,739,058

[45] Date of Patent: Apr. 19, 1988

[54] TETRA-(HYDROXYARYL)-BIS-QUINOXA-LINES AND PREPARATION THEREOF

[75] Inventors: Volker Eckhardt; Hans-Rudolf Dicke; Dieter Freitag, all of Krefeld, Fed. Rep. of Germany

[73] Assignee: Bayer Aktiengesellschaft, Leverkusen, Fed. Rep. of Germany

[21] Appl. No.: 876,160

[22] Filed: Jun. 19, 1986

[30] Foreign Application Priority Data

Jul. 5, 1985 [DE] Fed. Rep. of Germany ....... 3524054

[51] Int. Cl.$^4$ ........................................... C07D 241/36
[52] U.S. Cl. .................................. 544/353; 528/201; 528/203
[58] Field of Search ......................................... 544/353

[56] References Cited

U.S. PATENT DOCUMENTS

| | | | |
|---|---|---|---|
| Re. 27,682 | 6/1972 | Schnell et al. | 260/47 |
| 3,028,365 | 4/1962 | Schnell et al. | 260/47 |
| 3,062,781 | 11/1962 | Bottenbruch et al. | 260/47 |
| 3,534,040 | 10/1970 | Straley et al. | 260/267 |
| 3,702,326 | 11/1972 | Arnold | 260/250 R |
| 3,799,953 | 3/1974 | Freitag et al. | 260/395 |
| 3,852,244 | 12/1974 | Heath et al. | 260/50 |
| 3,897,392 | 7/1975 | Haupt et al. | 260/47 |
| 3,931,108 | 1/1976 | Binsack et al. | 260/47 |
| 3,966,729 | 6/1976 | Kovar et al. | 260/250 Q |
| 4,086,232 | 4/1978 | Kovar et al. | 260/250 Q |
| 4,125,725 | 11/1978 | Duffy | 544/353 |
| 4,185,009 | 1/1980 | Idel et al. | 260/45.9 |
| 4,393,190 | 7/1983 | Tyrell et al. | 528/170 |

FOREIGN PATENT DOCUMENTS 138015 10/1979 German Democratic Rep. .

*Primary Examiner*—Harold D. Anderson
*Attorney, Agent, or Firm*—Gene Harsh; Joseph C. Gil; Aron Preis

[57] ABSTRACT

The present invention relates to bis-quinoxalines of the formula I

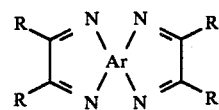

their preparation, their use as branching agents for the preparation of branched, thermoplastic polycarbonates and the branched thermoplastic polycarbonates.

13 Claims, No Drawings

TETRA-(HYDROXYARYL)-BIS-QUINOXALINES AND PREPARATION THEREOF

The present invention relates to bis-quinoxalines of the formula I

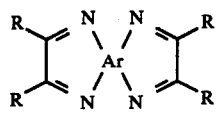

wherein
the radicals R independently of one another are 4-hydroxyaryl or 3-hydroxyaryl radicals which can carry one or more alkyl, alkoxy, aryl or halogen substituents,
and wherein
Ar is a tetravalent aromatic radical which preferably has 6 to 30 C atoms and can be mononuclear or polynuclear, it being possible for the polynuclear radicals to be fused and/or bridged, hetero atoms or carbonyl groups functioning as bridge members and it also being possible for the tetravalent Ar radicals to contain alkyl, alkoxy, aryl or halogen substituents.

Alkyl substituents in the present connection are preferably methyl, ethyl, n-propyl, iso-propyl, n-butyl, iso-butyl or tert.-butyl radicals; alkoxy substituents in the present connection are methoxy, ethoxy, n-propoxy, iso-propoxy, n-butoxy, iso-butoxy or tert.-butoxy radicals; aryl substituents are phenyl, tolyl, chlorophenyl or naphthyl radicals; and halogen substituents are fluorine, chlorine or bromine.

Suitable hydroxyaryl radicals R are hydroxyphenyl, cresyl, hydroxybiphenyl, hydroxymethoxyphenyl, hydroxychlorophenyl and hydroxynaphthyl.

Suitable tetravalent aromatic Ar radicals are phenylene, naphthylene, biphenylene, sulpho-bis-(phenylene), oxy-bis-(phenylene) and carbonyl-bis-(phenylene), and corresponding alkyl-substituted, alkoxy-substituted or halogen-substituted tetravalent aromatic Ar radicals.

Examples of radicals R are 4-hydroxyphenyl, 3-hydroxyphenyl, 4-hydroxy-3-methylphenyl, 4-hydroxy-2-methylphenyl, 3-hydroxy-5-methylphenyl, 5-hydroxy-2-biphenyl, 4-hydroxy-3-methoxyphenyl, 4-hydroxy-3-chlorophenyl and 4-hydroxynaphth-1-yl.

Examples of Ar radicals are 1,2,4,5-phenylene, 2,3,6,7-naphthylene, 3,3',4,4'-biphenylene, 2,2',3,3'-biphenylene, sulpho-bis-(3,4-phenylene), sulpho-bis-(2,3-phenylene), oxy-bis-(3,4-phenylene), oxy-bis-(2,3-phenylene), carbonyl-bis-(3,4-phenylene) and carbonyl-bis-(2,3-phenylene).

Examples of compounds of the formula I are 2,2',3,3'-tetra-(4-hydroxyphenyl)-6,6'-bis-quinoxaline, 2,2',3,3'-tetra-(3-hydroxyphenyl)-6,6'-bis-quinoxaline, 2,2', 3,3'-tetra-(4-hydroxyphenyl)-5,5'-bis-quinoxaline, 2,2', 3,3'-tetra-(3-hydroxyphenyl)5,5'-bis-quinoxaline, 6,6-sulphonyl-bis-(2,3-di-[4-hydroxyphenyl]-quinoxaline), 6,6'-sulphonyl-bis-(2,3-di-[3-hydroxyphenyl]-quinoxaline), 5,5'-sulphonyl-bis-(2,3-di-[4-hydroxyphenyl]-quinoxaline), 5,5'-sulphonyl-bis-(2,3-di-[3-hydroxyphenyl]-quinoxaline), 6,6'-oxy-bis-(2,3-di-[4-hydroxyphenyl]-quinoxaline), 6,6'-oxy-bis-(2,3-di-[3-hydroxyphenyl]-quinoxaline), 5,5'-oxy-bis-(2,3-di-[4-hydroxyphenyl]-quinoxaline), 5,5'-oxy-bis-(2,3-di-[3-hydroxyphenyl]-quinoxaline), 6,6'-carbonyl-bis-(2,3-di-[4-hydroxyphenyl]-quinoxaline), 6,6'-carbonyl-bis-(2,3-di-[3-hydroxyphenyl]-quinoxaline), 5,5'-carbonyl-bis-(2,3-di-[4-hydroxyphenyl]-quinoxaline), 5,5'-carbonyl-bis-(2,3-di-[3-hydroxyphenyl]-quinoxaline), 2,2',3,3'-tetra-(4-hydroxy-3-methylphenyl)-6-6'-bis-quinoxaline, 2,2',3,3'-tetra-(4-hydroxy-2-methylphenyl)-6,6'-bis-quinoxaline, 2,2',3,3'-tetra-(4-hydroxy-3-methoxy-phenyl)-6,6'-bis-quinoxaline, 2,2',3,3'-tetra-(4-hydroxy-2-methoxyphenyl)-6,6'-bis-quinoxaline, 2,2',3,3'-tetra-(4-hydroxy-3-chlorophenyl)-6,6'-bis-quinoxaline, 2,2',3,3' -tetra-(4-hydroxy-2-chlorophenyl)-6,6'-bis-quinoxaline, 2,2',3,3'-tetra-(6-hydroxy-3-biphenyl)-6,6'-bis-quinoxaline,

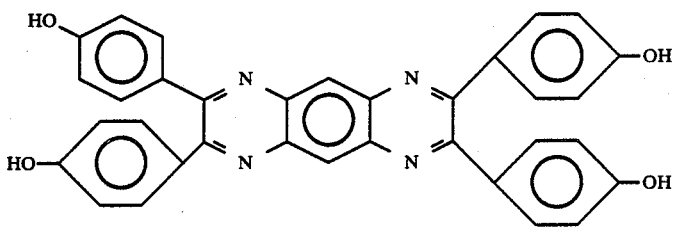

and

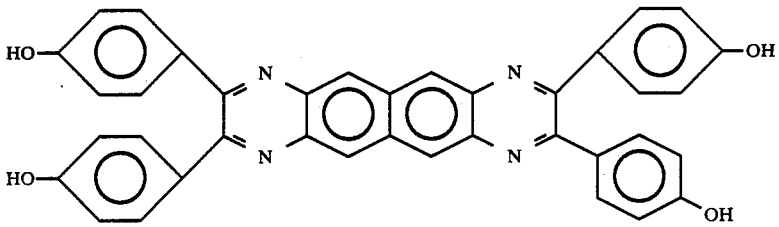

A preferred compound of the formula I is

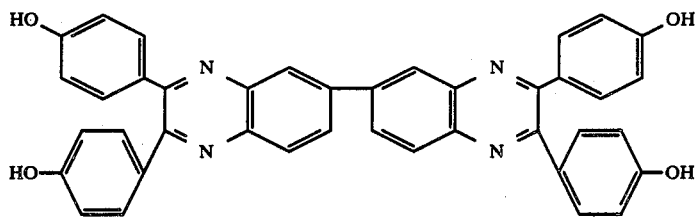

The new bis-quinoxalines of the formula I are prepared by reacting the corresponding tetraamino compounds of the formula II with the corresponding α-diketones of the formula III

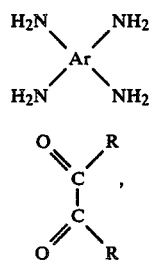

wherein

Ar and R have the meaning mentioned in the case of formula I, in a molar ratio of II:III of 1:2, at temperatures between 20° C. and 200° C., preferably between 40° C. and 100° C., it being possible, if appropriate, also to use an acid catalyst.

Solvents which can be used are lower alcohols, such as methanol, ethanol and isopropanol, aliphatic ethers, such as diethyl ether, cyclic ethers, such as tetrahydrofuran and dioxane, halogenohydrocarbons, such as chloroform, methylene chloride and 1,1-dichloroethane, or esters, such as, for example, ethyl acetate. The solvent is in each case chosen so that a sufficient solubility of the reactants, that is to say the tetraamino compound and the α-diketone, is ensured.

The reaction can be carried out in the absence of catalysts or can be catalysed by weak acids, such as acetic acid, propionic acid, benzoic acid or p-toluenesulphonic acid.

The reaction is preferably carried out by dissolving the α-diketone III in one of the abovementioned solvents and adding half the molar amount of tetra-amine II. After addition of the abovementioned catalysts in amounts of 0.001–0.1 mol %, based on the number of moles of II, the mixture is allowed to react for between 0.5 hour and 5 hours. The reaction product thereby precipitates. It can be isolated by filtration with suction. Purification is possible by dissolving in alkalis, such as dilute sodium hydroxide solution or ammonia solution, and subsequently precipitating the product in acids, or by recrystallization from the customary solvents, such as, for example, dioxane.

The present invention thus also relates to a process for the preparation of bis-quinoxalines of the formula I, which is characterized in that tetra-amines of the formula II are reacted with diketones of the formula III in a molar ratio of II:III of 1:2 in polar organic solvents at temperatures between 20° and 200° C. over a period of 0.5–5 hours, it being possible, if appropriate, to accelerate the reaction by addition of 0.001–0.1 mol %, based on the number of moles of II, of a catalyst.

Examples of suitable tetraamino compounds II are 1,2,4,5-tetraaminobenzene, 2,3,5,6-tetraaminopyridine, 1,2,5,6-tetraaminonaphthalene, 3,3',4,4'-tetraaminodiphenyl ether, 3,3'-diaminobenzidine, 3,3',4,4'-tetraminodiphenyl sulphone, 3,3',4,4'-tetraaminobenzophenone, 2,2',3,3'-tetraaminobiphenyl, 2,2',3,3'-tetraaminodiphenyl ether, 2,2',3,3'-tetraaminobenzophenone, 2,2',3,3'-tetraaminodiphenyl sulphone, 1,2,7,8-tetraaminonaphthalene and 2,3,6,7tetraaminonaphthalene. The preferred tetraamino compound is 3,3'-diaminobenzidine.

The tetraamino compounds II are either known from the literature (see, for example, WO 84/01161, pages 45–59), or they can be prepared by processes which are known from the literature.

Examples of suitable α-diketones III are 4,4'-dihydroxybenzil, 4,4'-dihydroxy-2,2'-dimethylbenzil, 4,4'-dihydroxy 2,2'-diethylbenzil, 4,4'-dihydroxy-2,2'-dipropylbenzil, 4,4'-dihydroxy-2,2'-diisopropylbenzil, 4,4'-dihydroxy-2,2'-dibutylbenzil, 4,4'-dihydroxy-2,2'-di-tert.-butylbenzil, 4,4'-dihydroxy-2,2'-diphenylbenzil, 4,4'-dihydroxy-2,2'-dichlorobenzil, 4,4'-dihydroxy-2,2'-dibromobenzil, 3,3'-dihydroxybenzil, 3,3'-dihydroxy-5,5'-dimethylbenzil, 3,3'-dihydroxy-5,5'-diethylbenzil, 3,3'-dihydroxy-5,5'-dipropylbenzil, 3,3'-dihydroxy-5,5'diisopropylbenzil, 3,3'-dihydroxy-5,5'-dibutylbenzil, 3,3'-dihydroxy-5,5'-di-tert.-butylbenzil, 3,3'-dihydroxy-5,5'-diphenylbenzil, 3,3'-dihydroxy-5,5'-dichlorobenzil, 3,3'-dihydroxy-5,5'-dibromobenzil, bis-1,2-(4-hydroxynaphth-1-yl)-ethanedione and bis-1,2-(6-hydroxynaphth-2-yl)-ethanedione. The preferred α-diketone is 4,4'-dihydroxybenzil.

The α-diketones III are likewise known from the literature or can be prepared by processes which are known from the literature.

The bis-quinoxalines I according to the invention are particularly suitable branching agents for the preparation of branched polycarbonates. The branched polycarbonates obtainable therefrom have a high stability under load of the melt strand (melt stability), so that they are also suitable for the production of large-volume hollow articles by the extrusion blow moulding process.

The present invention thus also relates to the use of the bis-quinoxalines of the formula I for the preparation of branched, thermoplastic aromatic polycarbonates.

The polycarbonates obtainable according to the invention are still soluble in the customary polycarbonate solvents, such as, for example, $CH_2Cl_2$.

The preparation of branched polycarbonates is known (see, for example, U.S. Reissue Pat. No. 27,682 (Le A 10 076-U.S.-CIP-Re), DE-OS (German Published Specification) 2,113,347 (Le A 13 638), DE-OS (German Published Specification) 2,254,918 (Le A 14 711), DE-OS (German Published Specification) 2,254,917 (Le A 14 719) and DE-OS (German Published Specification) 2,500,092 (Le A 16 142).

The bis-quinoxalines of the formula (I) can in principle be incorporated into the thermoplastic polycarbonates by all the three known polycarbonate preparation processes, by the phase boundary process, by the process in a homogeneous solution and by the melt transesterification process. The phase boundary process is the preferred process.

The polycarbonates branched with the bis-quinoxalines of the formula (I) according to the invention have marked structural viscosity properties, so that the same type of polycarbonate is particularly suitable for extrusion processing and for injection moulding processing. The branched polycarbonates obtainable according to the invention show a marked dependency of their apparent melt viscosity on the particular rate of deformation in the region of the deformation rates appropriate for extrusion processing and injection moulding processing. Their apparent melt viscosity is high at low deformation rates (extrusion) and low at high deformation rates (injection moulding processing).

The present invention thus also relates to a process for the preparation of branched, thermoplastic, aromatic polycarbonates from diphenols, 0.01 to 1 mol %, based on the number of moles of diphenols, of branching agents, 0.1 to 8.0 mol %, based on the number of moles of diphenols, of monophenolic chain stoppers and phosgene under the conditions of the phase boundary process or under the conditions of the process in a homogeneous solution, or from diphenols, 0.01 to 1 mol %, based on the number of moles of diphenols, of branching agents and 95 mol % to 120 mol %, based on the number of moles of diphenols, of carbonic acid diaryl esters under the conditions of the melt transesterification process, characterized in that bis-quinoxalines of the formula (I) are used as branching agents.

The present invention also relates to the branched thermoplastic, aromatic polycarbonates obtainable by the process according to the invention.

As is known, the conditions of the phase boundary process are the combination of an aqueous alkaline phase and an organic, water-immiscible phase which dissolves the polycarbonate formed, a suitable alkali being, for example, NaOH and suitable organic solvents being, for example, $CH_2Cl_2$ or chlorobenzene or mixtures of $CH_2Cl_2$ with chlorobenzene, reaction temperatures of between about 20° C. and 80° C. and the simultaneous use of tertiary amine catalysts, such as triethylamine or N-ethylpiperidine, or of quaternary ammonium salt catalysts, such as tetrabutylammonium bromide.

The amount of phosgene to be employed can be partly or completely replaced by other compounds which form carbonate groups under the reaction conditions of the phase boundary process, for example by mono- or bischlorocarbonic acid esters of the diphenols to be employed or by $COBr_2$.

The amount in moles of phosgene or two halogeno-CO group equivalents per phenolic OH group is between 45 and 90 mol %, preferably between 60 and 70 mol %.

As is known, the conditions of the process in a homogeneous phase are anhydrous mixtures of pyridine or other organic bases with organic polycarbonate solvents, such as $CH_2Cl_2$, and reaction temperatures of between about 20° C. and 80° C.

The amount of phosgene to be employed can, as described above, be partly or completely replaced by other compounds which form carbonate groups under the reaction conditions of the process, and approximately correspond to that in the phase boundary process.

In the known melt transesterification, the diphenols are likewise reacted with the carbonic acid diaryl esters in the presence of 0.01 to 1.0 mol % of branching agents and a basic catalyst, such as sodium bisphenolate, at temperatures from 150° to 300° C. and with application of a vacuum, the phenol component obtained during the transesterification simultaneously being distilled off, but it being ensured, by an appropriate reaction procedure, that the particular amount of monophenol of 0.1 to 8 mol % based on the number of moles of diphenol, required for chain stopping remains in the reaction melt and thus makes separate addition of monophenolic chain stoppers unnecessary. The polycarbonate obtained is isolated here via the melt without purification.

Carbonic acid diaryl esters which can be employed are, for example, diphenyl carbonate, di-(halogenophenyl) carbonates, such as di-(chlorophenyl) carbonate, di-(bromophenyl) carbonate, di-(trichlorophenyl) carbonate, di-(tribromophenyl) carbonate and the like, di-(alkylphenyl) carbonates, such as di-(tolyl) carbonate and the like, di-(naphthyl) carbonate, di-(chloronaphthyl) carbonate, phenyl tolyl carbonate, chlorophenyl chloronaphthyl carbonate or mixtures.

Examples of suitable monophenolic chain stoppers are phenol, m- and p-methylphenol, m- and p-ethylphenol, m- and p-propylphenol, m- and p-isopropylphenol, p-bromophenol, m- and p-butylphenol and p-tert.-butylphenol, the latter being preferred.

Examples of suitable diphenols are hydroquinone, resorcinol, 4,4'-dihydroxydiphenyl and bis-(hydroxyphenyl)-alkanes, -cycloalkanes, sulphides, ethers, ketones, sulphoxides or sulphones, furthermore, $\alpha,\alpha'$-bis-(hydroxyphenyl)-diisopropylloenzene and the corresponding nuclearalkylated or nuclear-halogenated compounds. Preferred diphenols are 4,4'-dihydroxy-2,2-diphenylpropane (bisphenol A), tetrachlorobisphenol A, tetrabromobisphenol A, tetramethylbisphenol A and mixtures of these compounds. Bisphenol A is particularly preferred.

Preferred mixtures consist of 80–99.5 mol %, preferably 90–98 mol %, of bisphenol A and 20–0.5 mol %, preferably 10–2 mol %, of tetrahalogenobisphenol A.

Other diphenols are described, for example, in U.S. Pat. Nos. 3,028,365 and 3,062,781.

To prepare the polycarbonates by the phase boundary condensation which is known per se, for example, the bis-quinoxaline of the formula (I) is dissolved in sodium hydroxide solution together with the diphenol component, and a water-immiscible solvent, such as, for example, methylene chloride, dichloroethane or chlorobenzene, is added. After introducing phosgene at room temperature, the polycarbonates according to the invention are isolated directly in high yields, with maximum incorporation of the branching agent, from the organic phase, after this has been washed, by distilling off the solvent or by precipitation. The chain length of the polycarbonates is adjusted by addition of the chain stopper. The polycondensation is additionally accelerated by tertiary amines, for example triethylamine.

In the solution condensation, which is likewise known in principle, for example, phosgenation is carried out in solution in the absence of water with at least twice the molar amount of pyridine, based on the phosgene employed, together with a cosolvent, such as methylene chloride. The corresponding pyridinium chloride and excess pyridine are removed by washing with dilute mineral acids and the polycarbonate solution obtained is worked up in the customary manner.

The thermoplastic, high molecular weight, soluble and branched polycarbonates obtainable according to the invention have relative viscosities $\eta_{rel}$ of 1.23–1.80 (measured on solutions of 0.5 g of product in 100 ml of methylene chloride at 25° C.), average molecular weights $\overline{M}_{LS}$ (measured by light scattering) of 10,000 to 200,00) and apparent melt viscosities of $5 \times 10^4$ to $10^2$ Pa.s (at 300° C. and at deformation rates of between $1s^{-1}$ and $5 \times 10^3 s^{-1}$).

with suction, recrystallized from dioxane and dried at 100° C. under a water pump vacuum.

| Yield: 53.3 g (= 85% of theory) $C_{40}H_{26}N_4O_4$ (626.67) | | | |
|---|---|---|---|
| Calculated | C 76.7 | H 4.18 | N 8.94% |
| Found | 76.6 | 4.07 | 8.98% |

2,2',3,3'-Tetra-(4-hydroxyphenyl)-6,6'-bis -quinoxaline, called quinoxalinetetraphenol in the following examples, corresponds to the formula

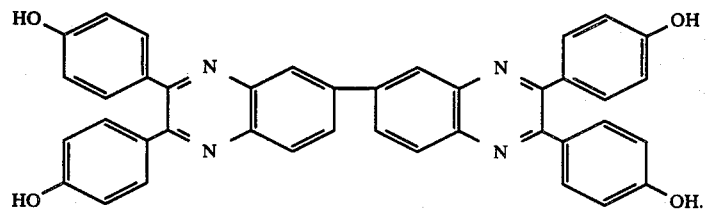

The customary additives for polycarbonates, for example dyestuffs, pigments, mould release agents, stabilizers against the action of moisture, heat and UV light, lubricants and fillers, such as glass powder, quartz products or graphite, molybdenum sulphide, metallic powders, powders of higher-melting plastics, such as polytetrafluoroethylene powder, natural fibres, such as cotton, sisal and asbestos, and furthermore glass fibres of the most diverse types, metal filaments and fibres which are stable during residence in the melt of the polycarbonates and do not noticeably damage the polycarbonates, can be added to the polycarbonates obtainable according to the invention before, during or after their preparation.

Because of the outstanding stability properties of the melt strand, the polycarbonates according to the invention are particularly suitable for the production of hollow articles by the blow moulding process. The excellent structural viscosity properties also allow, for example, extruded films with good mechanical properties and reduced stress cracking, which can be employed in the electrical and automobile sectors, to be obtained in a readily accessible manner.

Shaped articles and mouldings of all types, such as housings, spools, coverings, domestic appliances and the like, can be produced by injection moulding.

The percentage contents stated in the examples relate to the weight, unless indicated otherwise. The relative viscosities $\eta_{rel}$ were measured on 0.5% strength solutions in methylene chloride at 25° C. The apparent melt viscosities (dimension pascal . second (Pa.s)) at the particular deformation rate ($s^{-1}$) stated were determined at 300° C. Further details can be found in the examples.

EXAMPLES AND COMPARISON EXPERIMENTS

A: Preparation of 2,2', 3,3'-tetra-(hydroxyphenyl)-6,6'-bis-quinoxaline 48.8 g of 4,4'-dihydroxybenzil are dissolved in 300 ml of methanol, and 21.4 g of 3,3'-diaminobenzidine in 700 ml of methanol are added dropwise. The reaction mixture is first stirred at room temperature for 30 minutes, during which a yellow solid gradually precipitates. The reaction is brought to completion by heating under reflux for two hours. The reaction product is filtered off

B: BRANCHED AND NON-BRANCHED POLYCARBONATES

EXAMPLE 1

45.6 g of bisphenol A (BPA) and 0.125 g of quinoxalinetetraphenol (0.1 mol % of branching agent, based on bisphenol A) are dissolved in 680 g of 6.2% strength sodium hydroxide solution, under nitrogen. A solution of 0.677 g of phenol in 900 g of non-stabilized methylene chloride is added and 41.6 g of phosgene are passed into the entire reaction mixture at pH 12 to 13 in the course of 30 minutes at 25° C., with vigorous stirring. Thereafter, 0.2 g of triethylamine is added and the mixture is allowed to after-react for a further 1 hour. The organic phase is separated off and washed twice with 2% strength phosphoric acid and three times, or until the aqueous phase is free from electrolytes, with water. After the solvent has been distilled off, 43.2 g of polycarbonate with a relative viscosity $\eta_{rel}$ of 1.346 are obtained.

After heating the polycarbonate melt at 300° C. for minutes, no change was detectable in the solution viscosity. The branched polycarbonate is thus stable to heat.

EXAMPLE 2

45.6 g of BPA and 0.251 g of quinoxalinetetraphenol (0.2 mol % of branching agent, based on bisphenol A) are dissolved in 680 g of 6.2% strength sodium hydroxide solution, under nitrogen, and a solution consisting of 0.677 g of phenol and 900 g of non-stabilized methylene chloride is added. 41.6 g of phosgene are passed in at room temperature in the course of one hour, with intensive stirring (pH of the solution: 12–13). After addition of 0.2 g of triethylamine, the mixture is allowed to react further for another hour. When the alkaline phase is free from bisphenol A, the phases are separated and the organic phase is washed twice with 2% strength phosphoric acid and three times with water, or until no further electrolyte is detectable in the wash water. 42.9 g of branched polycarbonate are obtained from the organic phase after distilling off the solvent. $\eta_{rel} = 1.378$ $M_{Vis} = 38,700$ $M_{LS} = 105,000$ $M_{LS} =$ molecular weight, measured by light scattering

Comparison Experiment 1

A polycarbonate was prepared under the same conditions as in Example 2, but with the exception that no quinoxalinetetraphenol was added as the branching agent. $\eta_{rel}=1.256$ $M_{Vis}=26,500$ $M_{LS}=27,000$ Example 2 and Comparison Experiment 1 illustrate the high branching achieved by co-condensation of quinoxalinetetraphenol in the polycarbonate, as can be seen from the difference in the molecular weights determined via viscosity and light scattering measurement.

Example 3

22.8 g of bisphenol A, 22.7 g of diphenyl carbonate and 0.0626 g of quinoxalinetetraphenol (0.1 mol %, based on the bisphenol A) are melted together with 0.02 mg of sodium bisphenolate in an oxygen-free atmosphere, the temperature being increased from 200° C. to 300° C. and the pressure being reduced from 100 mm Hg to 1 mm Hg in the course of 5 hours. After the phenol formed in the transesterification has been distilled off, a transparent polycarbonate with a relative viscosity $\eta_{rel}=1.247$ is obtained.

Example 4

The dependence of the apparent melt viscosity on the shearing rate was determined at 300° C. (nozzle L/D=20) on the polycarbonates prepered in Example 2 and in Comparison Experiment 1 to illustrate the pronounced structural viscosity of the polycarbonates according to the invention.

| a. Polycarbonate according to Example 2 | | | | | |
|---|---|---|---|---|---|
| Rate of deformation (s$^{-1}$) | 10$^1$ | 5 × 10$^1$ | 10$^2$ | 5 × 10$^2$ | 10$^3$ |
| Apparent melt viscosity (Pa · s) | 3600 | 1900 | 1400 | 700 | 500 |
| b. Polycarbonate according to Comparison Experiment 1 | | | | | |
| Rate of deformation (s$^{-1}$) | 10$^1$ | 5 × 10$^1$ | 10$^2$ | 5 × 10$^2$ | 10$^3$ |
| Apparent melt viscosity (Pa · s) | 450 | 450 | 450 | 400 | 350 |

We claim:
1. A bis-quinoxaline of the general formula

wherein the R radicals independently one of the other denote 4-hydroxyaryl or 3-hydroxyaryl which are unsubstituted or substituted with one or more alkyl, alkoxy, aryl or a halogen substituent and Ar denotes a tetravalent mononuclear or polynuclear aromatic radical which is unsubstituted or substituted with one or more alkyl, alkoxy, aryl or a halogen substituent, said polynuclear radical being selected from the group consisting of fused rings and bridged rings and said bridged rings being bridged by at least one member selected from the group consisting of heteroatoms and carbonyl groups.

2. A bis-quinoxaline according to claim 1 in which aromatic radical Ar has 6 to 30 carbon atoms. tert.-butyl, methoxy, ethoxy, n-propoxy, isopropoxy, n-butoxy, isobutoxy, tert.-butoxy, phenyl, tolyl, chlorophenyl, naphthyl, fluorine, chlorine and bromine.

3. A bis-quinoxaline according to claim 1 in which the substituents on R are selected from the group consisting of methyl, ethyl, n-propyl, isopropyl, n-butyl, isobutyl, tert.-butyl, methoxy, ethoxy, n-propoxy, isopropoxy, n-butoxy, isobutoxy, tert.-butoxy, phenyl, tolyl, chlorophenyl, naphthyl, flourine, chlorine and bromine.

4. A bis-quinoxaline according to claim 1 in which the radicals R are chosen from hydroxy-phenyl, cresyl, hydroxybiphenyl, hydroxymethoxyphenyl, hydroxychlorophenyl or hydroxynaphthyl.

5. A bis-quinoxaline according to claim 1 in which Ar is a tetravelent aromatic radical chosen from phenylene, naphthylene, biphenylene, sulpho-bis-(phenylene), oxybis-(phenylene or carbonyl-bis-(phenylene).

6. The compound of the formula

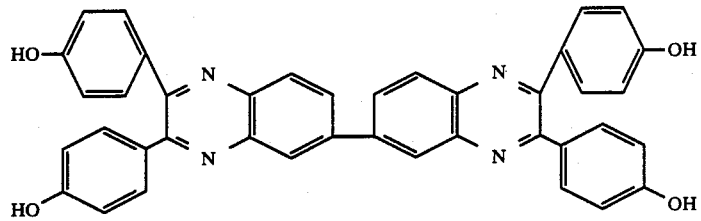

7. The bis-quinoxaline of claim 1 wherein the substituents of said Ar are selected from the group consisting of methyl, ethyl, n-propyl, isopropyl, n-butyl, isobutyl, 8. A process for the production of a bis-quinoxaline of claim 1, in which a tetraamine of the general formula

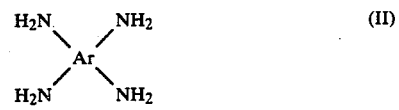

in which
Ar has the same meaning as in claim 1, is reacted with a diketone of the general formula

in which
R has the same meaning as in claim 1, in a molar ratio of (II) : (III)=1:2 in a polar organic solvent at a temperature between 20° and 200° C. over a period of 0.5–5 hours.

9. A process according to claim 8, in which the reaction is accelerated by the addition of 0.001 to 0.1 mol %, based on the number of moles of the compound of formula (II), of an acid catalyst.

10. A process according to claim 9, in which the catalyst is selected from acetic acid, propionic acid, benzoic acid or p-toluene-sulphonic acid.

11. A process according to claim 8, in which the reaction is carried out at a temperature between 40° C. and 100° C.

12. A process according to claim 9 in which the solvent is selected from methanol, ethanol, isopropanol, diethyl ether, tetrahydrofuran, dioxane, chloroform, methylene chloride, 1,1-dichloroethane or ethyl acetate.

13. A bis-quinoxaline produced by the process of claim 8.

* * * * *